United States Patent [19]

Cioca

[11] Patent Number: 4,515,637
[45] Date of Patent: May 7, 1985

[54] COLLAGEN-THROMBIN COMPOSITIONS

[75] Inventor: Gheorghe Cioca, Coatesville, Pa.

[73] Assignee: Seton Company, Newark, N.J.

[21] Appl. No.: 552,110

[22] Filed: Nov. 16, 1983

[51] Int. Cl.$^3$ .................. C08L 89/06; A61K 35/14; C08H 1/06
[52] U.S. Cl. ..................... 424/94; 106/124; 106/161; 424/14; 514/801
[58] Field of Search .............. 424/101, 359, 28; 106/124, 161, 122

[56] References Cited

U.S. PATENT DOCUMENTS

| | | | |
|---|---|---|---|
| 3,928,566 | 12/1975 | Briggs | 424/101 |
| 4,271,070 | 6/1981 | Miyata et al. | 106/161 |
| 4,412,947 | 11/1983 | Cioca | 106/124 |
| 4,414,976 | 11/1983 | Schwarz et al. | 106/161 |
| 4,442,655 | 4/1984 | Stroetmann | 424/101 |

OTHER PUBLICATIONS

Derwent Abstract: South African Application No. 82/0123, Nov. 1982, Eberhard Zimmerman et al.

Primary Examiner—Theodore Morris
Attorney, Agent, or Firm—Webb, Burden, Robinson & Webb

[57] ABSTRACT

A method of forming a collagen-thrombin hemostatic composition is comprised of forming a homogeneous aqueous admixture of collagen and thrombin at a basic pH and lyophilizing the collagen-thrombin admixture to form a stable collagen sponge having thrombin therein. The collagen utilized in the process is absorbable when placed in vivo. Additionally, a lyophilized collagen product is comprised of collagen which is absorbable when placed in vivo and thrombin distributed within the collagen. The collagen product is storage stable.

10 Claims, No Drawings

COLLAGEN-THROMBIN COMPOSITIONS

BACKGROUND OF THE INVENTION

1. Field of the Invention

This invention relates to collagen-thrombin compositions, and more particularly to collagen-thrombin compositions which are storage stable.

2. Description of the Prior Art

"Natural insoluble collagen" as used herein means and refers to collagen which cannot be dissolved in an aqueous alkaline or in any inorganic salt solution without chemical modification, and includes hides, splits and other mammalian or reptilian coverings. More particularly, natural insoluble collagen means and refers to the corium which is the intermediate layer of a bovine hide between the grain and the flesh sides.

In young animals there is little intermolecular and interfibrillar crosslinking which provides for some degree of solubility of the collagen.

"Native collagen" as used herein means and refers to collagen, whether natural insoluble collagen or soluble collagen, wherein the quaternary structure of the protein has been preserved.

Collagen constitutes the connective tissue and is the major type of fibrous protein in higher vertebrae. Collagen in its natural state exists in a triple chain helix along with a constant periodicity between aligned triple chains. The triple helical configuration of collagen is sometimes referred to as a fibril and the fibrils align with an axial periodicity of about 640 Å.

Although there are several types of collagen, the major type is referred to as "type I" which is the major collagen of skin, bones and tendons. The type I collagen has a chain composition of $[\alpha 1(I)_2 \alpha 2]$. The $\alpha 1(I)$ and $\alpha 2$ chains are homologous.

The use of collagen in substantially pure form has been proposed for many uses, including burn dressings, as disclosed in U.S. Pat. Nos. 3,939,831 and 3,514,518, and similar medical applications are disclosed in U.S. Pat. Nos. 3,157,524 and 3,628,974.

Among the many uses of collagen which have been proposed in the prior art is its use as a hemostat. Collagen has been known to promote the coagulation of blood along with a healing promotion. One of the advantages of collagen when used as a hemostat or implantation into the body is that the collagen dissolves due to enzymatic digestion and other biological processes. This is due primarily to the nativity of the collagen, and thus, when collagen is to be implanted in the body, it is desired that it maintain its nativity.

Further, it has been recognized that local stoppage of bleeding and tissue bonding can be achieved with blood clotting factors such as thrombin. Several compositions which include thrombin as a blood coagulant have been proposed, such as are disclosed in U.S. Pat. Nos. 2,433,299 and 4,363,319. It is recognized that thrombin in dry form is storage stable when supplied in sealed containers. In order to utilize such thrombin it must be removed from the container and used immediately. Thrombin, per se, had limited use as a blood coagulant because of problems with handling and stability. In its most desirable form, thrombin is incorporated into a pad or substrate of some kind so that it can be applied to the wound. Many attempts, both successful and unsuccessful, have been made in order to provide a storage stable thrombin pad or substrate for utilization in external coagulation areas. With respect to implantable materials, the combination of collagen and thrombin would appear to be ideal for the healing of internal wounds, particularly useful during surgery and the like. The collagen can be utilized as a carrier for the thrombin, and collagen pads or the like with the thrombin impregnated herein can be applied to the wound to promote coagulation with the subsequent digestion of the collagen in the biological system.

For the most part, these efforts have been limited to incorporating stabilized thrombin solutions of unstabilized thrombin solutions into collagen fabrics, pads or the like. However, these thrombin-containing substrates must be used immediately since storage stability has presented a problem. Further, in the thrombin-impregnated collagen substrate the thrombin is mobile so there is a potential for seepage of the thrombin into a particular organ when the impregnated pad is utilized in surgery. Exemplary of collagen-thrombin combinations are those compositions disclosed in South African Application No. 820123 entitled "Material for Sealing and Healing of Wounds." Thus, it has been desired by those workers in the art to provide a thrombin-impregnated collagen substrate wherein the thrombin is immobile and is not capable of migration into a particular organ, and further, where such composition is storage stable.

BRIEF DESCRIPTION OF THE INVENTION

A method of forming a collagen-thrombin hemostatic composition is comprised of forming a homogeneous aqueous admixture of collagen and thrombin at a basic pH and lyophilizing the collagen-thrombin admixture to form a stable collagen sponge having thrombin therein. The collagen utilized in the process is absorbable when placed in vivo. Additionally, a lyophilized collagen product is comprised of collagen which is absorbable when placed in vivo and thrombin distributed within the collagen. The collagen product is storage stable.

DETAILED DESCRIPTION OF THE INVENTION

The collagen useful in the practice of the invention is a collagen which is capable of being dissolved due to enzymatic digestion and through other biological processes in vivo. Most preferably, the collagen is native collagen either in potentially soluble form or natural insoluble collagen which is inherently crosslinked and insoluble in either acid or a basic media.

In addition, collagen which has been treated in such a manner as to make it water dispersible or soluble can also be utilized so long as when it is reconstituted it retains its quanternary structure, and thus, its capability of dissolution in vivo due to enzymatic digestion and through other biological processes. The natural insoluble collagen useful in the practice of the invention is such as is disclosed in U.S. patent application Ser. No. 382,133, filed May 26, 1982 entitled "Collagen Sponge" of Gheorghe Cioca, now U.S. Pat. No. 4,412,947, incorporated herein by reference and made a part hereof.

The native collagen which is not crosslinked and is useful in the practice of the invention is one which has its crosslinked interfibrillar bonds between individual polypeptide chains severed while maintaining its quaternary structure and is soluble in at least acidic media. A typical process for preparing such collagen is disclosed in U.S. Pat. No. 4,279,812, issued July 21, 1981 of Gheorghe Cioca entitled "Process For Preparing Macromolecular Biologically Active Collagen." Other methods known to those skilled in the art for preparing dispersible or soluble collagen can also be utilized, so long as the nativity of the collagen is retained.

The thrombin useful in the practice of the invention can be human, porcine, bovine or equine in origin. The thrombin can be prepared by methods well known to those skilled in the art and is typically prepared by production from prothrombin.

In order to prepare the collagen useful in the practice of the invention, the particular collagen is dispersed in water and typically in an acidic media to effect adequate dissolution or dispersion. The dispersion is preferably at a solids concentration of 0.1 to about 0.6 percent by weight collagen in water. Subsequent to the dispersion of the collagen, it is preferably, but not necessarily, first dialyzed against distilled water to remove salts therefrom and then again dialyzed against a sodium hydroxide aqueous solution to provide a pH on the basic side. The second or pH dialysis is preferred in order to maintain sterilization and, additionally, to have a more controlled conversion of the acidic collagen solution to the basic side. Typically, the pH of the collagen solution is about 7.1 to about 8.0 after dialysis. The collagen is normally dialyzed against sodium hydroxide, potassium hydroxide or a similar base in aqueous solution at a level of about 0.05 to about 3 Normal. After dialysis, the thrombin powder in pure form is added and agitated with the aqueous collagen dispersion or solution until homogeneous.

The thrombin powder is incorporated at a level of about 300 units or greater of thrombin to 0.1 gram of collagen. Below this level it has been found that the collagen articles do not provide sufficient hemostatic properties to be particularly effective. There is no maximum amount of thrombin that can be included in the solution; however, up to 11,000 units of thrombin to 0.1 gram of collagen has been found to be particularly effective.

Subsequent to the formation of a homogeneous dispersion or solution of the collagen-thrombin admixture, the solution or dispersion is placed in an appropriate container, such as a tray or a dish, and freeze-dried. Although freeze-drying processes well known to those skilled in the art may be utilized, a freeze-drying process whereby there is some cryogenic destruction of the collagen bonds forming free radicals is particularly desirable. This particular freeze-drying process is such that the collagen-thrombin solution is frozen to reduce its temperature at a rate of $-18°$ L C. to $-24°$ C./hour until it is at a temperature of $-60°$ C. to $-70°$ C. The frozen solution is then placed in a freeze-dryer with an initial temperature of $-60°$ C. to $-70°$ C. and vacuum sublimated at $10^{-3}$ to $10^{-5}$ torr. The freeze-drying process requires about 12 to 24 hours with a final temperature of $30°$ C. Freeze-drying processes wherein the final temperature of the collagen solution if $-20°$ C. prior to vacuum sublimation are also acceptable.

After the collagen solution has been freeze-dried and rendered free of moisture, it is in the form of a collagen sponge having thrombin distributed throughout.

The collagen product so produced is storage stable and is particularly effective as a hemostat, particularly where the hemostat must remain inside the body. Thus, during surgical operations the collagen product is placed on the particular incision and wound to stop bleeding and can remain in contact with the wound and be internal to the body. Over time the collagen article or sponge dissolves due to enzymatic digestion or other biological processes.

The invention can be more fully understood, although not to be limited, by the following examples:

EXAMPLE 1

Thirty milliliters of collagen solution prepared in accordance with Example I of U.S. Pat. No. 4,279,812 were charged to an appropriate vessel. The collagen solution had a solids content of 0.2 percent by weight. The collagen solution was dialyzed against distilled water to remove any residual salts therefrom. Subsequent to the dialysis against distilled water, the collagen solution was again dialyzed against 0.1 Normal aqueous sodium hydroxide to a pH of 7.2. Subsequent to the second dialysis, 0.2 gram of substantially pure thrombin powder representing 6,600 units of thrombin was charged to the collagen solution and agitated until apparent homogeneity had resulted. The collagen solution was charged to a tray and frozen at a temperature of $-60°$ C. to $-70°$ C. to effect a temperature reduction rate of the collagen of $-20°$ C./hour to a temperature of $-60°$ C. The collagen was then freeze-dried with an initial temperature of $-60°$ C. and had a final temperature of $30°$ C. after 16 hours. After storage for one week at ambient temperature under sterile conditions, the collagen article was tested and found to contain 7,000 units of thrombin which represented somewhat above the theoretical recovery of the starting thrombin.

EXAMPLE 2

Thirty milliliters of 0.2 percent collagen dispersion of crosslinked native collagen prepared in accordance with Example I of U.S. patent application Ser. No. 382,133 were dialyzed against distilled water to remove salts therefrom and again dialyzed against 0.1 Normal sodiun hydroxide solution to a pH of 7.2. The thrombin powder was added at the same level and in accordance with the procedure of Example 1 and the product was freeze-dried in accordance with Example 1. After storage of the collagen article produced in accordance with Example 2 hereof, the article was tested and found to contain effectively the same number of thrombin units as had been originally introduced during the preparation of the collagen article.

EXAMPLE 3

Example 1 was repeated, except that it was not dialyzed and was at a level of 0.3 percent solids and adjusted to a pH of 7.2 with 0.1 Normal sodium hydroxide and a phosphate buffer was incorporated therein. 0.1 gram of thrombin powder was incorporated into the collagen solution, as in Example 1, and the solution was freeze-dried in accordance with Example 1. The collagen article so produced after storage was tested for thrombin activity and showed 3,147 units of thrombin, approximately the same amount as had been previously added.

It is important to note that the collagen product in accordance with the invention requires no additional stabilizers to retain its stability, and further, due to the immobilization and fixation of the thrombin on the collagen it has particular utility for use as an internal hemostat.

Although the invention has been described with respect to specific materials and specific processes, it is only to be limited so far as is set forth in the accompanying claims.

I claim:

1. A method of forming a collagen-thrombin hemostatic composition consisting essentially of:
   forming a homogeneous aqueous admixture of collagen and thrombin at a basic pH, wherein the ratio of collagen to thrombin is about 0.1 gram of collagen to about 300 units or greater of thrombin; and
   lyophilizing said collagen-thrombin admixture to form a stable collagen sponge having thrombin distributed uniformly throughout and wherein said collagen is absorbable when placed in vivo.

2. The method of claim 1 wherein said collagen-thrombin aqueous admixture is at a pH of about 7.1 to about 8.0.

3. The method of claim 1 wherein the aqueous admixture is about 0.1 to about 0.6 percent by weight collagen.

4. The method of claim 1 wherein said collagen is native collagen.

5. The method of claim 1 wherein said collagen is natural insoluble collagen.

6. A lyophilized collagen product, active ingredients consisting essentially of collagen which is absorbable when placed in vivo and thrombin distributed uniformly throughout said collagen, said product being storage stable.

7. The collagen product of claim 6 wherein said collagen is in the form of a sponge.

8. The collagen product of claim 6 wherein the ratio of collagen to thombin is about 0.1 gram of collagen to about 300 units or greater of thrombin.

9. The collagen product of claim 6 wherein said collagen is natural insoluble collagen.

10. The collagen product of claim 6 wherein said collagen is native collagen.

* * * * *